US012661202B2

(12) United States Patent
Chuang et al.

(10) Patent No.: US 12,661,202 B2
(45) Date of Patent: Jun. 23, 2026

(54) PACKAGING FOR A BLOOD GLUCOSE MONITOR

(71) Applicant: PLUME DESIGN, INC., Palo Alto, CA (US)

(72) Inventors: Meng-Jung Chuang, Taipei City (TW); Liem Hieu Dinh Vo, San Jose, CA (US); Christina Xu, Palo Alto, CA (US)

(73) Assignee: PLUME DESIGN, INC., Palo Alto, CA (US)

( * ) Notice: Subject to any disclaimer, the term of this patent is extended or adjusted under 35 U.S.C. 154(b) by 405 days.

(21) Appl. No.: 18/365,147

(22) Filed: Aug. 3, 2023

(65) Prior Publication Data

US 2025/0041016 A1     Feb. 6, 2025

(51) Int. Cl.
| | |
|---|---|
| *A61B 50/30* | (2016.01) |
| *A61B 5/00* | (2006.01) |
| *A61B 5/145* | (2006.01) |
| *A61B 50/20* | (2016.01) |

(52) U.S. Cl.
CPC .......... *A61B 50/30* (2016.02); *A61B 5/14532* (2013.01); *A61B 5/6826* (2013.01); *A61B 50/20* (2016.02)

(58) Field of Classification Search
CPC ..... A61B 50/30; A61B 50/20; A61B 5/14532; A61B 5/6826
USPC ........................ 206/303, 363, 438, 566, 6.1
See application file for complete search history.

(56) References Cited

U.S. PATENT DOCUMENTS

| | | | | |
|---|---|---|---|---|
| 3,197,166 A | * | 7/1965 | Sandler | A47F 7/02 |
| | | | | 248/500 |
| 4,880,117 A | * | 11/1989 | Garganese | B65D 73/0085 |
| | | | | 206/487 |
| 5,148,920 A | * | 9/1992 | Walker | A61F 2/0095 |
| | | | | 206/592 |
| 5,379,895 A | * | 1/1995 | Foslien | A61B 50/30 |
| | | | | 206/363 |
| 5,445,263 A | * | 8/1995 | Mohlenkamp | B65D 1/36 |
| | | | | 206/445 |
| 5,535,878 A | * | 7/1996 | Reed | A47F 7/02 |
| | | | | 206/493 |
| 5,547,072 A | * | 8/1996 | Kaiser | B65D 43/24 |
| | | | | 206/6.1 |

(Continued)

*Primary Examiner* — Jacob K Ackun
(74) *Attorney, Agent, or Firm* — Nicholas Martin; Greenberg Traurig, LLP

(57)     ABSTRACT

A packaging system for retaining an annular shaped unit in a vertically aligned position relative to a base plane, the packaging system may include a carrier base including a first receptacle, and a retaining member including a second receptacle and a wedge, the wedge being configured to retain the annular shaped unit in the second receptacle in the vertically aligned position, the retaining member being arranged in the first receptacle. The first receptacle may include a bottom surface having a concave shape corresponding to a shape of the annular shaped unit. The packaging system may also include a container including a base member and a top member. The base member being adapted to receive the carrier base therein, and the top member being configured to receive the base member therein, the container being configured to fully contain the carrier base, retaining member, and annular shaped unit therein.

19 Claims, 7 Drawing Sheets

(56) References Cited

U.S. PATENT DOCUMENTS

| | | | | |
|---|---|---|---|---|
| 5,868,253 A * | 2/1999 | Krueger | ................. | A61F 2/0095 |
| | | | | 206/583 |
| 6,588,585 B1 * | 7/2003 | Allen-Carpenter | .... | A45C 11/16 |
| | | | | 84/95.2 |
| 7,325,940 B2 * | 2/2008 | Cea | ......................... | A47F 3/001 |
| | | | | 362/104 |
| 2007/0034538 A1 * | 2/2007 | Landis | .................. | A61F 2/0095 |
| | | | | 206/363 |
| 2009/0200183 A1 * | 8/2009 | Dussin | ...................... | A47F 7/03 |
| | | | | 206/6.1 |
| 2012/0132546 A1 * | 5/2012 | De Lecce | ............... | A47F 7/024 |
| | | | | 206/6.1 |

* cited by examiner

200

200

PACKAGING FOR A BLOOD GLUCOSE MONITOR

FIELD

The present disclosure relates to the field of packaging. More particularly, to packaging for a blood glucose monitor.

BACKGROUND

Blood glucose monitors often include a sensor device for measuring analytes in the body of a user. The blood glucose monitor may also include a computing device which sends and receives measurements from the sensor device. The computing device may electrically communicate with the sensor device through a wired connection or through a wireless protocol such as, for example, using Bluetooth. Shipping and transportation of the blood glucose monitor requires retaining features to retain the sensor device and computing device in their respective positions to reduce the likelihood of damage from shipping. However, such features can add expense and complexity to the manufacturing process and can lead to a frustrating experience for consumers when removing the product for use.

SUMMARY

Some embodiments of the present disclosure relate to a packaging system for retaining an annular shaped unit in a vertically aligned position relative to a base plane, the packaging system including a carrier base including a first receptacle, and a retaining member. The retaining member includes a second receptacle and a wedge, the wedge being configured to retain the annular shaped unit in the second receptacle in the vertically aligned position relative to the base plane. Additionally, the retaining member being arranged in the first receptacle.

In some embodiments, the second receptacle includes a first bottom surface including a concave shape corresponding to the annular shaped unit and configured to enable the annular shaped unit to fully seat into the second receptacle.

In some embodiments, the retaining member is formed of a material including rubber or silicon.

In some embodiments, the retaining member is formed of a material consisting of rubber or silicon.

In some embodiments, the wedge is configured to engage an inner surface of the annular shaped unit to retain the annular shaped unit in the vertically aligned position.

In some embodiments, the packaging system is configured to receive any of a plurality of annular shaped units having different arc lengths and different heights.

In some embodiments, the packaging system further includes a container, the container including a base member including a bottom surface, and at least one first sidewall extending from the bottom surface and defining a first opening therein. The base member being configured to receive the carrier base therein. The container also includes a top member including a top surface, and at least one second sidewall extending from the top surface and defining a second opening therein. The top member being configured to receive the base member therein such that the at least one second sidewall extends around the at least one first sidewall when the top member is positioned onto the base member. The container being configured to fully contain the carrier base, the retaining member, and the annular shaped unit therein.

In some embodiments, the top member further includes a third receptacle, the third receptacle being configured to be collinearly aligned with the first receptacle and the second receptacle when the carrier base is arranged into the base member and the top member is positioned onto the base member.

In some embodiments, the third receptacle includes a second bottom surface including a concave shape corresponding to a shape of the annular shaped unit and configured to enable the annular shaped unit to fully seat into the third receptacle.

In some embodiments, a packaging system for a blood glucose monitor unit including a ring shaped body including any of a plurality of different arcs and different heights, the packaging system including a container, a carrier base including a first receptacle, and a retaining member including a second receptacle, the second receptacle includes a first bottom surface having a concave shape corresponding to a shape of the ring shaped body and configured to enable the blood glucose monitor unit fully seat into the second receptacle, and a wedge, and the container being configured to fully contain the carrier base, the retaining member, and the blood glucose monitor unit therein.

In some embodiments, the wedge being configured to act on an inner surface of the ring shaped body to retain the blood glucose monitor unit in a vertically aligned position relative to a base plane.

In some embodiments, the retaining member is formed of a material including rubber or silicon.

In some embodiments, the retaining member is formed of a material consisting of rubber or silicon.

In some embodiments, the first receptacle being configured to receive the retaining member therein.

In some embodiments, the container includes a base member including a bottom surface, and at least one first sidewall extending from the bottom surface, and a top member including a top surface, and at least one second sidewall extending from the top surface, the top member being configured to receive the base member therein such that the at least one second sidewall extends around the at least one first sidewall when the top member is positioned onto the base member.

In some embodiments, the top member further includes a third receptacle, the third receptacle being configured to be collinearly aligned with the first receptacle and the second receptacle when the carrier base is arranged into the base member and the top member is positioned onto the base member.

In some embodiments, the third receptacle includes a second bottom surface including the concave shape corresponding to the shape of the ring shaped body and configured to enable the blood glucose monitor unit to fully seat into the third receptacle.

In some embodiments, a method of packaging a blood glucose monitor unit including an annular shaped body having an inner circumference, the method including inserting a retaining member into a first receptacle of a carrier base, the first receptacle configured to hold the retaining member in a first position, and inserting the blood glucose monitor unit into a second receptacle of the retaining member until a wedge extending from a sidewall of the second receptacle is positioned within an aperture of the annular shaped body of the blood glucose monitor unit to hold the blood glucose monitor unit in the first position.

In some embodiments, the method further includes inserting the carrier base into a base member, and positioning a top member onto the base member so that the top member extends around a circumference of the base member and a third receptacle arranged on an inner surface of the top member is collinearly aligned with the first receptacle and the second receptacle to retain the blood glucose monitor unit in the first position.

In some embodiments, the top member and the base member fully contain the carrier base, the retaining member, and the blood glucose monitor unit therein.

BRIEF DESCRIPTION OF THE DRAWINGS

Some embodiments of the disclosure are herein described, by way of example only, with reference to the accompanying drawings. With specific reference now to the drawings in detail, it is stressed that the embodiments shown are by way of example and for purposes of illustrative discussion of embodiments of the disclosure. In this regard, the description taken with the drawings makes apparent to those skilled in the art how embodiments of the disclosure may be practiced.

DETAILED DESCRIPTION

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Various embodiments of the present disclosure relate to a packaging system for a sensor device having an annular shaped body, the packaging system including a carrier base including a first receptacle used to receive and hold a retaining member therein. The retaining member includes a second receptacle used to receive and hold the sensor device, and also includes a wedge arranged on a sidewall of the second receptacle configured to act upon an inner circumference of the sensor device to retain the sensor device in the second receptacle in a vertically aligned position relative to a base plane. The retaining member may be formed from a material such as, for example, rubber or silicon. In this regard, the material forming the retaining member may be capable of substantially retaining its shape while also having adequate elasticity to enable the sensor device to be inserted into the second receptacle such that the wedge member is positioned in the inner circumference of the sensor device.

The sensor device being packaged may come in any of a plurality of different sizes having different arc sizes and different heights. In various embodiments, the packaging system is adapted to accommodate any of the plurality of differently sized sensor devices. For example, the sensor device may be a size 6 ring or a size 14 ring. However, it is to be appreciated by those having ordinary skill in the art that the size of the sensor device that the packaging system is adapted to receive is not intended to be limiting and the sensor device being packaged therein may include any of a plurality of different shapes and sizes in accordance with the present disclosure.

Figure 1:
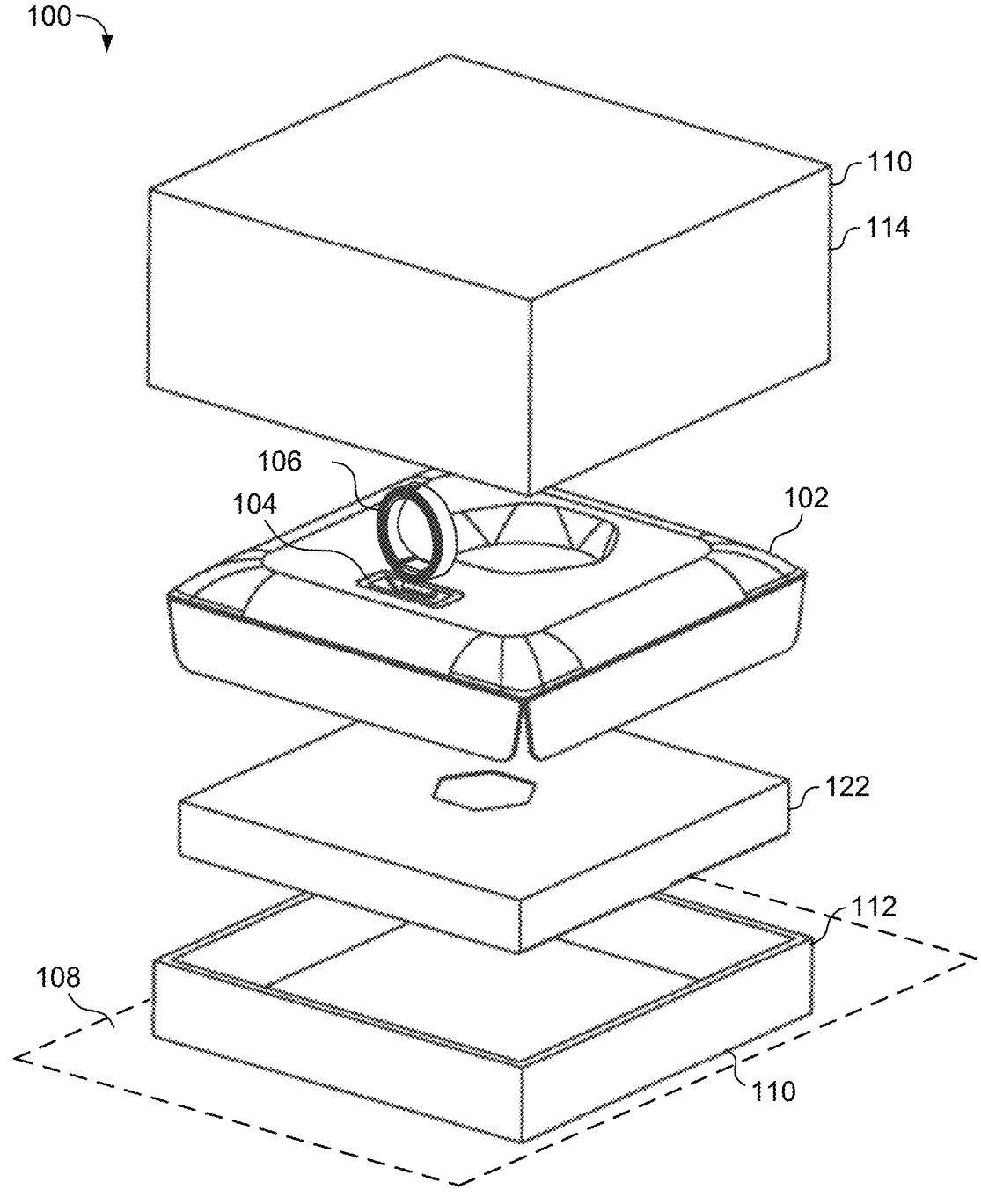
FIG. 1 is a non-limiting example of a packaging system, according to some embodiments.
Figure 2:
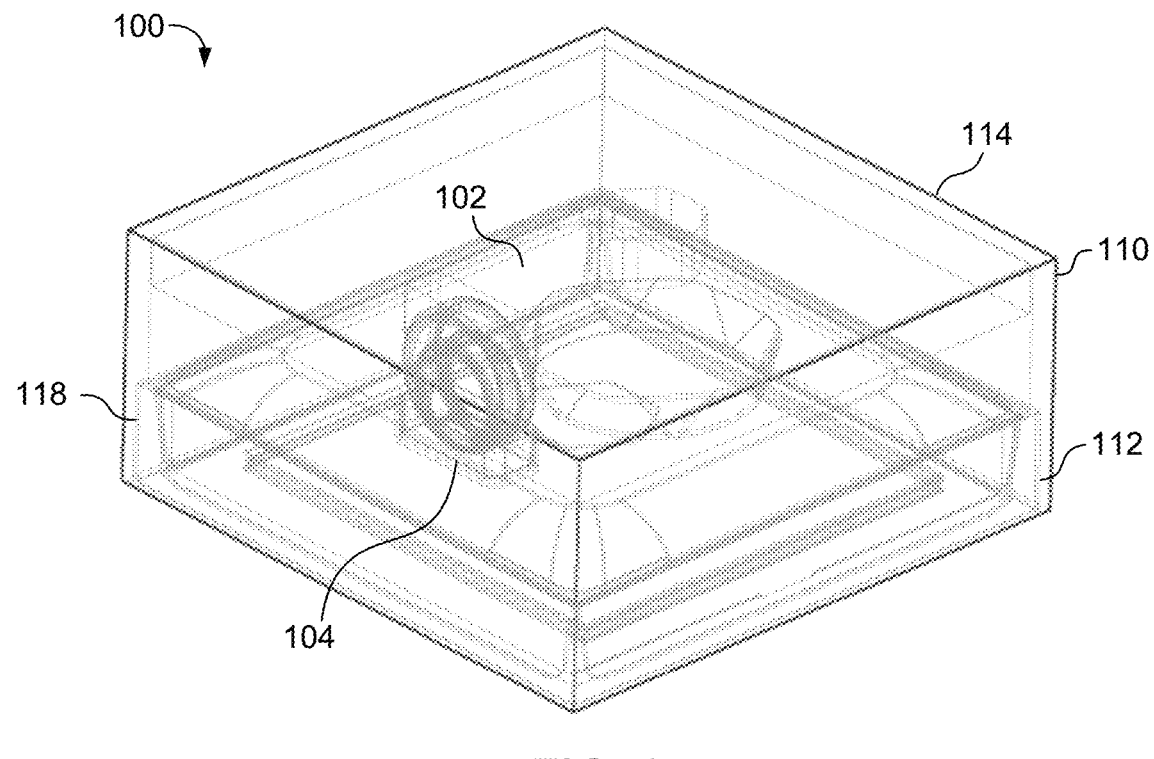
FIG. 2 is an exposed perspective view of the packaging system, according to some embodiments.
Figure 3:
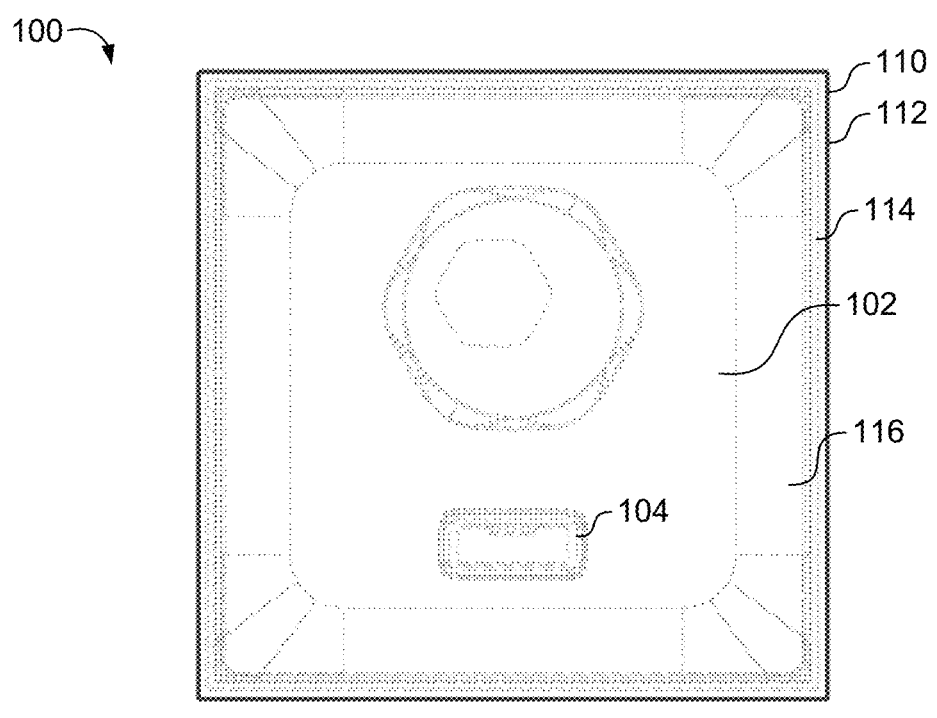
FIG. 3 is an exposed bottom view of the packaging system, according to some embodiments.
Figure 4:
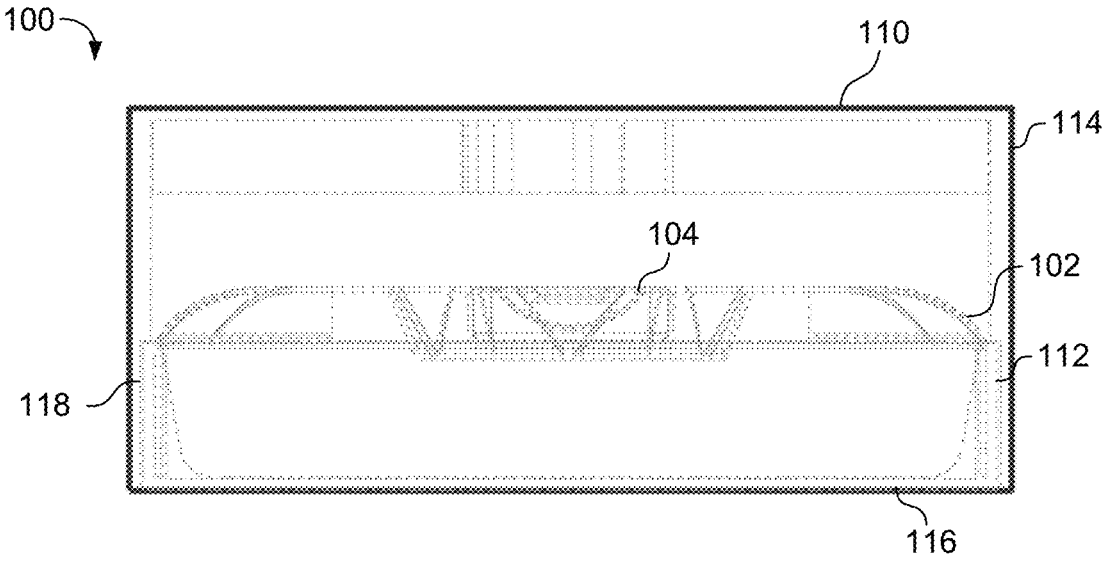
FIG. 4 is an exposed side view of the packaging system, according to some embodiments.

FIG. 1 illustrates a perspective view of a non-limiting example of a packaging system 100, according to some embodiments. FIG. 2 illustrates an exposed perspective view of the packaging system 100, according to some embodiments. FIG. 3 illustrates an exposed bottom view of the packaging system 100, according to some embodiments, FIG. 4 illustrates an exposed side view of the packaging system 100, according to some embodiments. Unless specifically referenced, FIGS. 1-3 will be described collectively.

The packaging system 100 includes a carrier base 102 and a retaining member 104 adapted to retain a position of a sensor device 106 in a vertically aligned position relative to a base plane 108. The sensor device 106 may also be referred to as an annular shaped unit or a blood glucose monitor unit having a ring-shaped body. In some embodiments, the sensor device 106 may an analyte monitoring device such as for example, a continuous glucose monitoring system or analyte monitoring system, for non-invasively monitoring analytes in an extremity of an individual and is capable of monitoring and outputting analyte concentration levels on demand. For example, the sensor device 106 may be worn around a digit of a hand. The sensor device 106 typically includes a body having an annular shape (e.g., ring-shaped body) and one or more modules for transmitting and/or receiving electromagnetic waves. In some embodiments, the sensor device 106 may include one or more modules embedded within the annular body for transmitting and receiving the electromagnetic wave signals, the first module in electronically communicable connection with a processing unit configured to control an operation of the first module, to store and process the signals relating to a permittivity of the digital arteries, and to estimate an analyte level or concentration based on the estimated permittivity.

Referring to FIG. 2, in some embodiments, the packaging system 100 may further include a container 110 adapted to fully contain the carrier base 102, the retaining member 104, and the sensor device 106 therein. The container 110 may include a base member 112 and a top member 114. Referring to FIG. 4, the base member 112 includes a surface 116 and at least one sidewall 118 extending from the surface 116. The surface 116 defines a bottom surface of base member 112 and extends on a plane parallel to a base plane 108. The at least one sidewall 118 extending from the surface 116 defines an opening opposite the surface 116, such as for receiving the carrier base 102 therein. The carrier base 102 is adapted to be arranged in an interior portion defined by the surface 116 and the at least one sidewall 118 of the base member 112. The base member 112 receives the carrier base 102 and the top member 114 may be arranged onto the base member 112 such that the top member 114 covers the opening of the base member 112 and substantially surrounds one or more sides of the base member 112. The base member 112 and top member 114 thereby act in cooperation to fully contain the carrier base 102, retaining member 104, and sensor device 106 within the container 110.

In some embodiments, the packaging system 100 may further include an insert 122 adapted to be positioned between the carrier base 102 and the base member 112 when installing the carrier base 102 into the base member 112. The insert 122 may be adapted to provide structural support to the carrier base 102 to enable the carrier base 102 to retain the position of the sensor device 106 in a fixed position when being packaged and when the packaging system 100 is being shipped. Additionally, in some embodiments, the insert 122 may define a bottom surface of the receptacles formed in the carrier base 102, as will be further described herein.

The insert 122 may be a layer of the material of the base member 112 and/or the carrier base 102 which is offset from the surface 116 to enable the insert 122 to provide support to the carrier base 102 and the sensor device 106 and/or the computing device installed into the carrier base 102 during packaging and shipping and for retaining a space between the sensor device 106 and/or the computing device and the surface 116 to prevent those components from being damaged due to the structural integrity of the container 110 being compromised.

Figure 5:
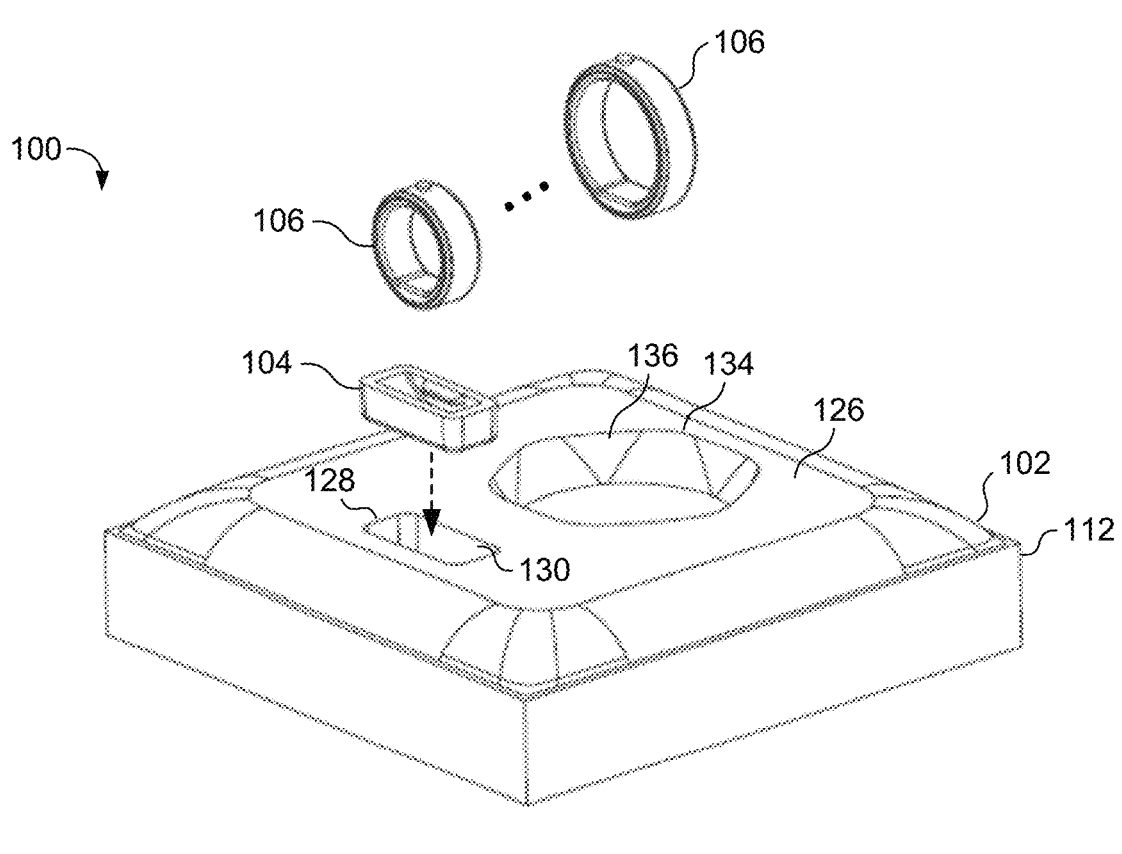
FIG. 5 is a perspective view of the carrier base, according to some embodiments.
Figure 6:
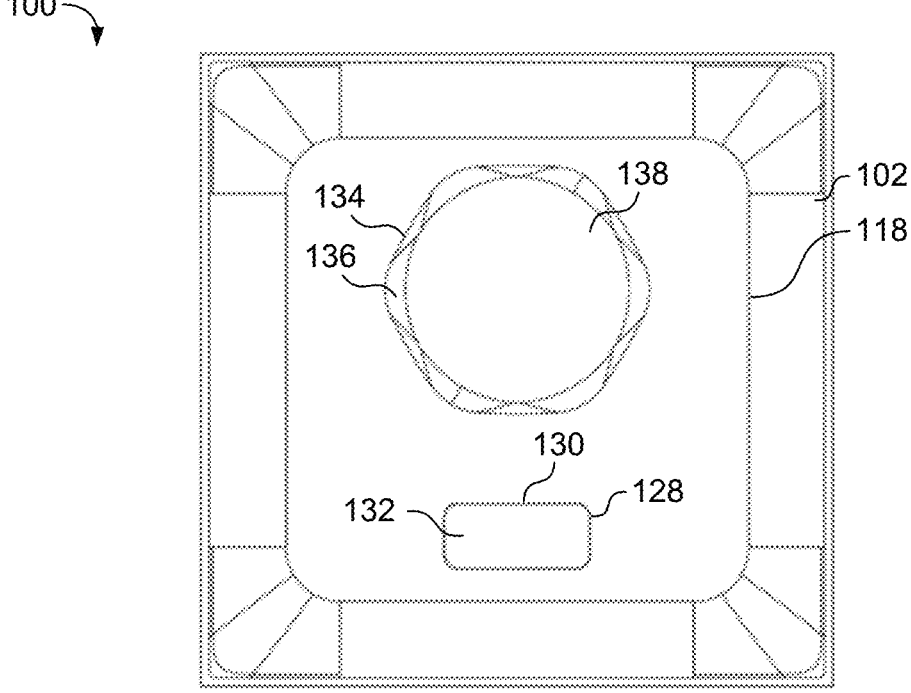
FIG. 6 is a top view of the carrier base, according to some embodiments.

FIG. 5 illustrates a perspective view of the carrier base 102, according to some embodiments. FIG. 6 illustrates a top view of the carrier base 102, according to some embodiments. Unless specifically referenced, FIGS. 5 and 6 will be described collectively.

The carrier base 102 includes a surface 126 and a first receptacle 128 arranged on the surface 126 which defines an opening on surface 126. The first receptacle 128 is adapted to receive and hold the retaining member 104 therein for retaining the position of the sensor device 106 when installed into the retaining member 104, as will be further described herein.

The first receptacle 128 may include one or more sidewalls 130 defining an interior portion of the first receptacle 128. In some embodiments, the first receptacle 128 may include a second opening formed at a bottom of the first receptacle 128. In other embodiments, the first receptacle 128 may include a surface 132 that defines a bottom of the first receptacle 128, such as shown in FIG. 6. In some embodiments, the surface 132 may be formed by a second layer of the carrier base 102 arranged below the layer of surface 126. In other embodiments, the surface 132 may be formed by the insert 122 arranged between the carrier base 102 and the base member 112.

In some embodiments, the carrier base 102 may include a fourth receptacle 134 arranged on the surface 126. The fourth receptacle 134 may include a shape and corresponding dimensions adapted to receive a computing device (not shown) that is packaged with the sensor device 106 and is configured to be placed in electrically communicable connection with the sensor device 106. In this regard, the fourth receptacle 134 may include any of a plurality of dimensions for accommodating the computing device therein to retain the position of the computing device within the packaging system 100.

The fourth receptacle 134 may include one or more sidewalls 136 defining an interior region of the fourth receptacle 134. In some embodiments, the fourth receptacle 134 may include an opening formed at a bottom of the fourth receptacle 134. In other embodiments, the fourth receptacle 134 may include a surface 138 defining the bottom of the fourth receptacle 134, such as shown in FIG. 6. In some embodiments, the surface 138 may be formed by a second layer of carrier base 102 located below surface 126. In other embodiments, the surface 138 may be formed by the insert 122 arranged between the carrier base 102 and the base member 112. In some embodiments, the insert 122 may further include an aperture extending therethrough arranged at the bottom opening of the fourth receptacle 134 in collinearly alignment with the fourth receptacle 134 and which is adapted to accommodate the computing device, or a portion thereof, in the aperture to enable the computing device to sit in the aperture such that the computing device sits in the fourth receptacle 134 at a lower height than if the fourth receptacle 134 was placed onto surface 138 therein.

Figure 7:
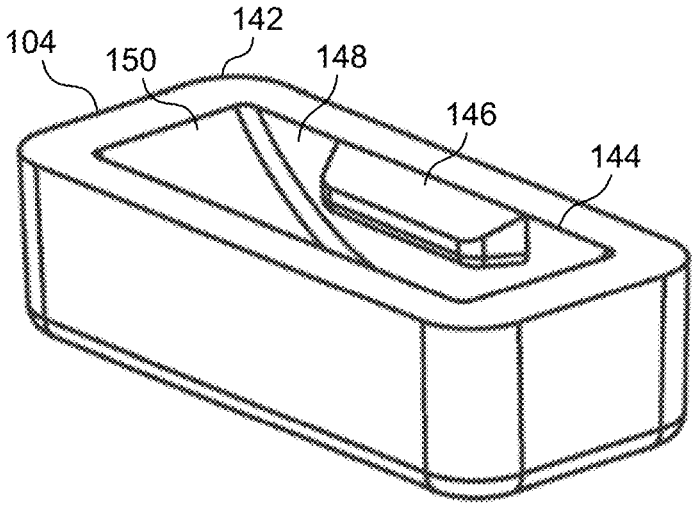
FIG. 7 is a perspective view of the retaining member, according to some embodiments.

FIG. 7 illustrates a perspective view of the retaining member 104, according to some embodiments.

The retaining member 104 includes a body 142. The retaining member 104 includes a second receptacle 144 and a wedge 146 defined by the body 142. The second receptacle 144 may include at least one sidewall 148 defining the interior region of the second receptacle 144. The second receptacle 144 is adapted to receive and hold the sensor device 106 in a vertically aligned position relative to the base plane 108 when the retaining member 104 and sensor device 106 are installed into the first receptacle 128. The wedge 146 extends from one of the at least one sidewall 148 towards an opposite side of the second receptacle 144. The wedge 146 is adapted to be positioned relative to the sensor device 106 when the sensor device 106 is installed into the second receptacle 144 such that the wedge 146 extends through an aperture of the sensor device 106 defined by an inner surface. As such, the wedge 146 helps retain and hold the sensor device 106 in the vertically aligned position relative to the base plane 108 when the sensor device 106 is installed into the second receptacle 144. In some embodiments, the wedge 146 may act upon or engage an inner surface of the annular shaped body (e.g., ring shaped body) of the sensor device 106 to retain and hold the sensor device 106 in the second receptacle 144 and in the vertically aligned position.

The second receptacle 144 may further include therein a surface 150 defining a bottom of the second receptacle 144. In some embodiments, the surface 150 may be a flat surface. In other embodiments, the surface 150 may be a concave surface, and which may correspond to a shape of the sensor device 106 to enable the second receptacle 144 to receive the sensor device 106 and to fully seat into the second receptacle 144. Additionally, in certain embodiments, the shape of the surface 150 may help improve retention and holding of the sensor device 106 in position therein. For example, the surface 150 having a concave shape may improve retention of the sensor device 106 by allowing the sensor device 106 to fully seat into the second receptacle 144 and the complementary shape may apply increased frictional force onto the sensor device 106, thereby retaining the orientation of the sensor device 106 from when the sensor device 106 was installed into the packaging system 100. As such, the concave shape of the surface 150 may enable the sensor device 106 to fully seat in the second receptacle 144 and helps limit rotation of the sensor device 106 within the second receptacle 144 from the orientation the sensor device 106 was originally installed into the second receptacle 144. In this regard, when the packaging system 100 is opened by a consumer or user of the sensor device 106, the orientation of the sensor device 106 in the packaging system 100 is the same as when the sensor device 106 was installed into the second receptacle 144 therein by a manufacturer. The ability to maintain a consistent orientation during shipping and transportation of the packaging system 100 and the sensor device 106 located therein may reduce the likelihood of accidentally damaging the sensor device 106 as a result of vibration or other external forces being applied to the packaging system 100 and the sensor device 106. In some embodiments, maintaining the orientation of the sensor device 106 in the packaging system 100 may also be desirable by the manufacturer as the sensor device 106 may be oriented such that a label or other identifier on the sensor device 106 may be observable by the consumer or user when they remove the top member 114 from the base member 112 and reveal the sensor device 106 within the container 110 and the packaging system 100.

The body 142 and the second receptacle 144 may include dimensions capable of receiving and holding a sensor device 106 having any of a plurality of different sizes. In this regard, the sensor device 106 may include a plurality of different arc lengths and different heights based on the ring size. Accordingly, the second receptacle 144 and the wedge 146 may act in cooperation with each other to help retain the position of the sensor device 106 having any of a plurality of different sizes in the second receptacle 144.

In some embodiments, the retaining member 104 may be one of a plurality of retaining members 104, each one of the plurality of retaining members 104 configured to receive and hold a sensor device 106 of a certain size or range of sizes therein. In this regard, in some embodiments, the retaining member 104 selected to be installed into the packaging system 100 may be one selected from a plurality of retaining members 104 based on the corresponding size and shape of the sensor device 106 being installed into the packaging system 100. Accordingly, the physical dimensions of the retaining member 104 in packaging system 100, and the corresponding size and dimensions of the second receptacle 144 and wedge 146 may also vary based on the size and shape of the sensor device 106 being packaged, and the retaining member 104 being installed into the packaging system 100 may be selected based on the size of the sensor device 106 also being installed therein. For example, the retaining member 104 selected for installation into the carrier base 102 may include appropriate dimensions for the second receptacle 144 to receive a size 6 ring therein, whereas a differently sized retaining member 104 having appropriate dimensions for the second receptacle 144 may need to be selected to receive a size 8 ring therein to ensure the sensor device 106 is packaged into the packaging system 100 and the packaging system 100 retains the sensor device 106 in the vertically aligned position and that axial rotation of the sensor device 106 during packaging and shipping is limited.

The body 142 may be made of a soft material. The body 142 may be made of a material capable of withstanding a certain amount of mechanical deformation forces and substantially returning to its original shape when the mechanical deformation forces being applied to the retaining member 104 are removed. The body 142 may also be made of a material having adequate elasticity to enable the sensor device 106 to be inserted into the second receptacle 144 such that the wedge 146 is positioned in the aperture of the sensor device 106.

The material forming the body 142 and the wedge 146 may include adequate rigidity to fixedly retain the sensor device 106 in the second receptacle 144 to prevent the sensor device 106 from falling out of the second receptacle 144 during packaging and installation, and while preventing the sensor device 106 from inadvertently rotating relative to its central axis in response to vibrational forces resulting from the packaging, shipping, and transportation of the packaging system 100 and the sensor device 106 located therein.

The retaining member 104 may be made any of a plurality of materials including rubber or silicon. In some embodiments, the retaining member 104 may be made of rubber. In other embodiments, the retaining member 104 may be made of silicon. In certain embodiments, the retaining member 104 may be made of a material consisting essentially of rubber and/or silicon. In other embodiments, the retaining member 104 may be made of a material consisting of rubber and/or silicon.

Figure 8:
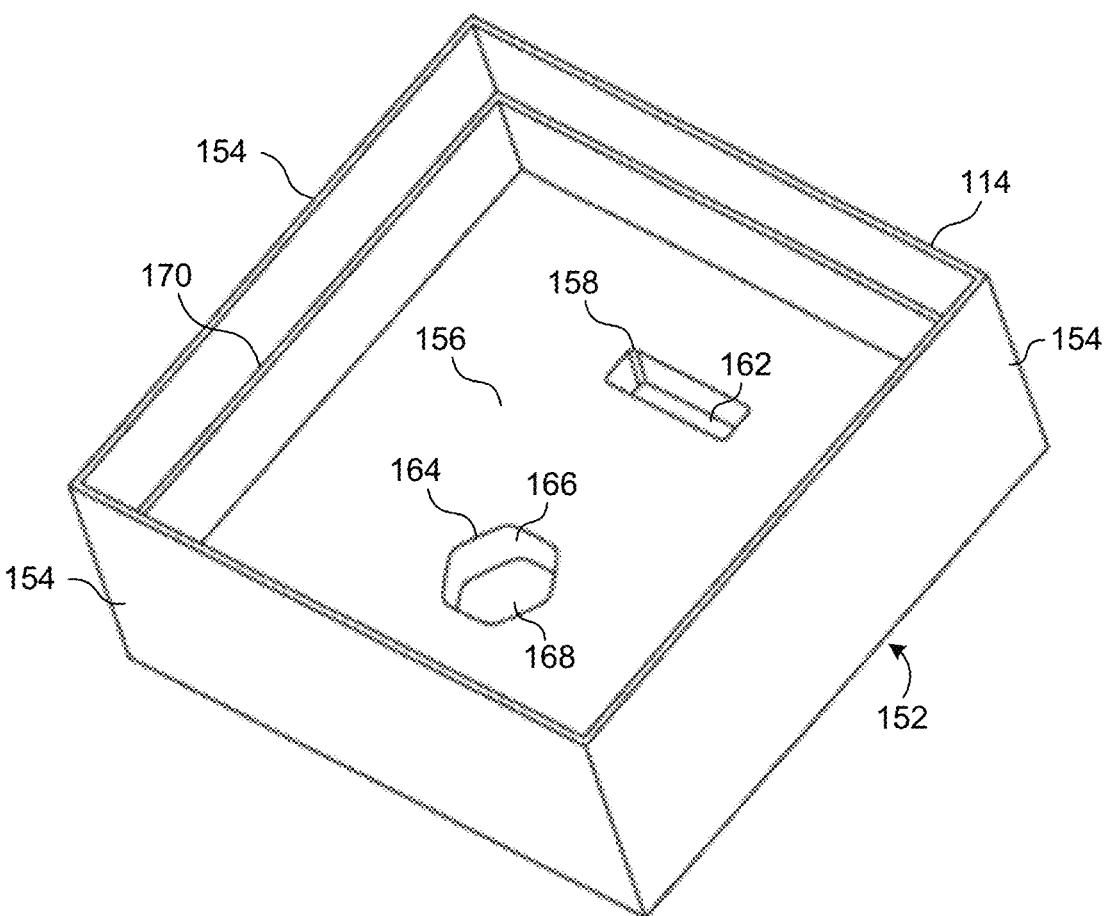
FIG. 8 is a perspective view of the top member, according to some embodiments.
Figure 9:
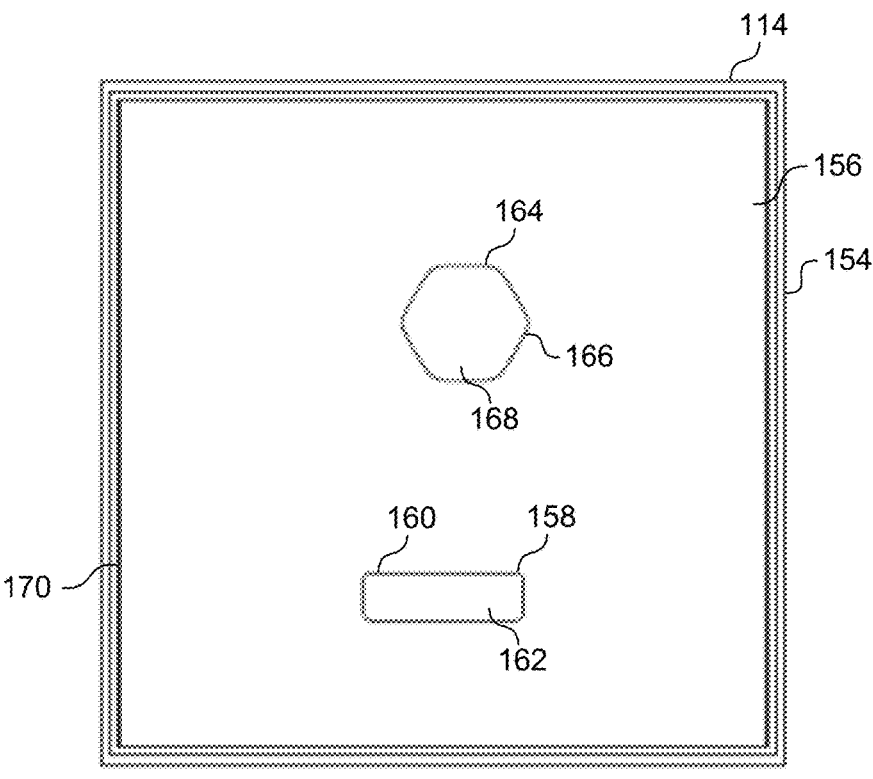
FIG. 9 is a bottom view of the top member, according to some embodiments.
Figure 10:
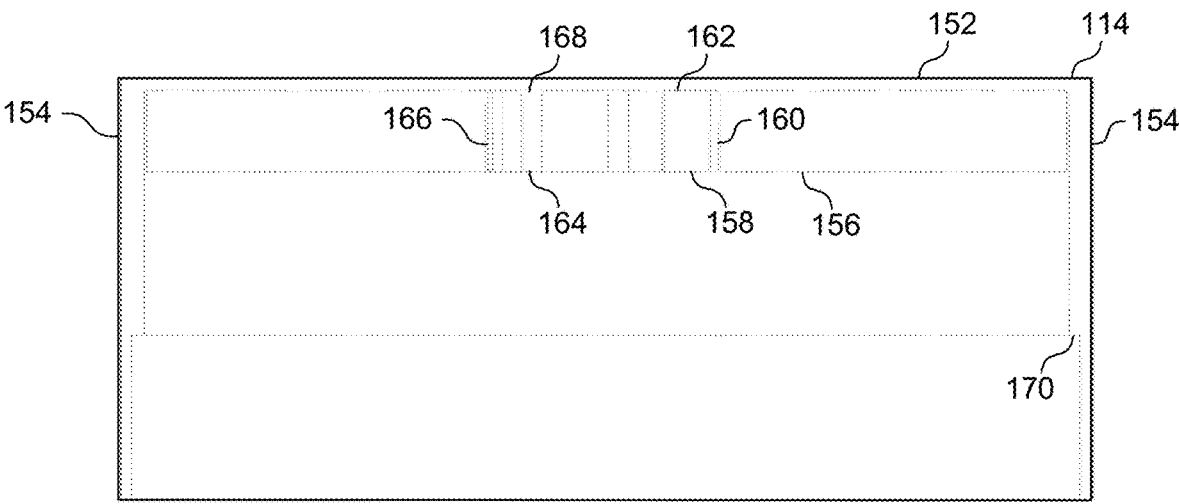
FIG. 10 is an exposed side view of the top member, according to some embodiments.

FIG. 8 illustrates a perspective view of the top member 114, according to some embodiments. FIG. 9 illustrates a bottom view of the top member 114, according to some embodiments. FIG. 10 illustrates an exposed side view of the top member 114, according to some embodiments. Unless specifically referenced, FIGS. 8-10 will be described collectively.

Unless stated otherwise, the top member 114 will be described according to the orientation of the top member 114 as illustrated in FIG. 8. The top member 114 includes a surface 152 and at least one sidewall 154 extending therefrom. The surface 152 extends along a plane that is substantially parallel to base plane 108 when the top member 114 is positioned onto base member 112 and encloses the carrier base 102, retaining member 104, and sensor device 106 therebetween. The at least one sidewall 154 extend from the surface 152 and defines an opening therebetween which is adapted to receive the base member 112 into the opening when the top member 114 is positioned onto the base member 112, thereby enclosing therein the carrier base 102, retaining member 104, and sensor device 106. In some embodiments, the top member 114 may include a surface 156 formed at an interior region of the top member 114. The surface 156 may be a layer of the material of the top member 114 offset from the surface 152 to enable the surface 156 to provide support to the sensor device 106 and/or the computing device installed within the packaging system 100 during packaging and shipping and for retaining a space between the sensor device 106 and/or the computing device and the surface 152 to prevent those components from being damaged due to the structural integrity of the container 110 being compromised.

Additionally, in some embodiments, the top member 114 may include a third receptacle 158 arranged in the interior region of the top member 114 on the surface 156 and extending towards the surface 152. The third receptacle 158 may include one or more sidewalls 160 defining the interior of the third receptacle 158. The third receptacle 158 may also include a surface 162 at a bottom of the third receptacle 158. In some embodiments, the surface 152 may define the bottom of the third receptacle 158.

In some embodiments, the surface 162 at the bottom of the third receptacle 158 may be a flat surface. In other embodiments, the surface 162 at the bottom of the third receptacle 158 may be a concave surface that corresponds to the shape of the body of the sensor device 106 such as to enable the top member 114 to be installed onto the base member 112 and retain the position of the sensor device 106 installed into the retaining member 104 and the second receptacle 144. As such, the top member 114 may be adapted to be installed onto the base member 112 such that the third receptacle 158 is collinearly aligned with the first receptacle 128 and the second receptacle 144 for holding the sensor device 106 in the packaging system 100 in a fixed position during packaging and shipping.

Additionally, in some embodiments, the top member 114 may further include a fifth receptacle 164 arranged in the top member 114 on the surface 156 and extending towards the surface 152. The fifth receptacle 164 may include one or more sidewalls 166 defining the interior of the fifth receptacle 164. In some embodiments, the fifth receptacle 164 may include a surface 168 at a bottom of the fifth receptacle 164. In some embodiments, the surface 152 may define the bottom of the third receptacle 158. The fifth receptacle 164 is adapted to receive the top of the computing device (not shown) when the top member 114 is installed onto the base member 112. As such, the top member 114 is adapted to be installed onto the base member 112 and relative to the carrier base 102 such that the fifth receptacle 164 is collinearly aligned with the fourth receptacle 134 for holding the computing device in a fixed position in the packaging system 100 during packaging and shipping.

The top member 114 may include dimensions such that the at least one sidewall 154 is configured to slidingly extend around the base member 112 and the at least one sidewall 118 to fully contain the carrier base 102, the retaining member 104, and the sensor device 106 and/or the computing device therein. As such, the length and width of the base member 112 may be smaller than the length and width of the top member 114 to enable the top member 114 to be installed onto and around the base member 112. Additionally, in some embodiments, the top member 114 may further include a step 170 extending along at least a portion of an interior of the at least one sidewall 154. In some embodiments, the step 170 may extend along one or more of the at least one sidewalls 154. In other embodiments, each of the at least one sidewall 154 may include a step 170 thereon. The step 170 is adapted to enable the top member 114 to be positioned onto the top member 114 while retaining the longitudinal position of the base member 112 relative to the top member 114. In this regard, the at least one sidewall 118 of the base member 112 is configured to abut the step 170 when the top member 114 is installed onto the base member 112 such that a fixed distance between the base member 112 and top member 114 is maintained.

Figure 11:
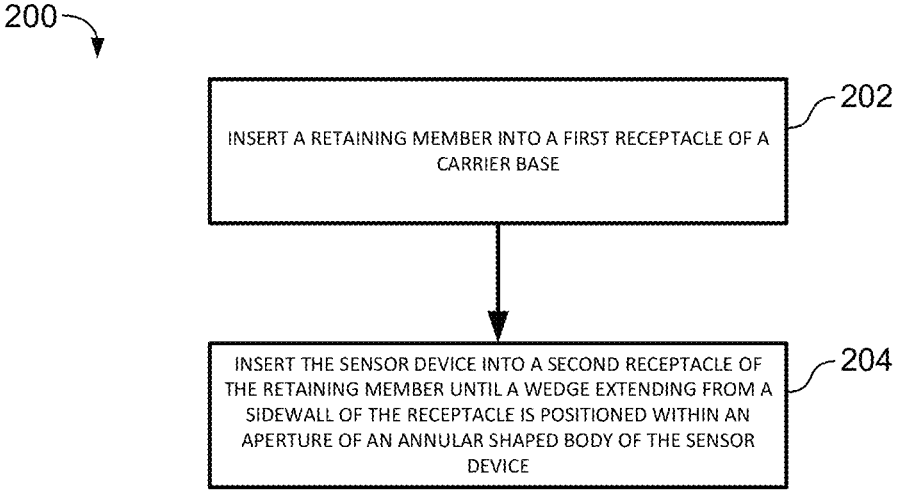
FIG. 11 is a flow diagram of a method, according to some embodiments.

FIG. 11 illustrates a flow diagram of a method 200, according to some embodiments.

The method 200 includes, at 202, inserting a retaining member 104 into a first receptacle 128 of a carrier base 102, the first receptacle 128 being configured to hold the retaining member 104 in a first position. In some embodiments, the first position is a vertically aligned position relative to a base plane 108.

The method 200 includes, at 204, inserting the sensor device 106 into a second receptacle 144 of the retaining member 104 until a wedge 146 extending from one of the at least one sidewall 148 of the second receptacle 144 is positioned within an aperture of an annular shaped body of the sensor device 106 in the first position. In some embodiments, the sensor device 106 may be referred to as a blood glucose monitor unit.

Figure 12:
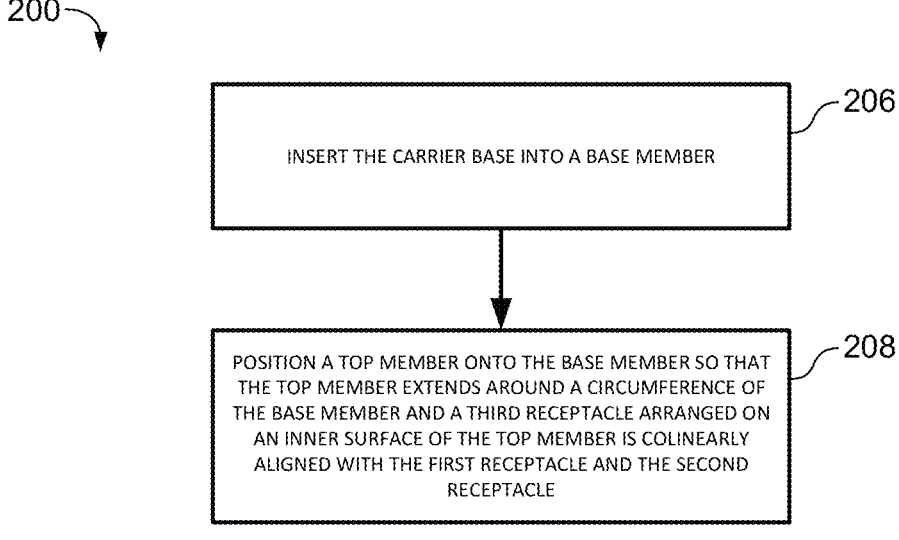
FIG. 12 is a second flow diagram of the method, according to some embodiments.

FIG. 12 illustrates a second flow diagram of the method 200, according to some embodiments.

In some embodiments, the method 200 further includes, at 206, inserting the carrier base 102 into a base member 112. In some embodiments, the method 200 further includes, at 208, positioning a top member 114 onto the base member 112 so that the top member 114 extends around a circumference of the base member 112 and a third receptacle 158 arranged on an inner surface of the top member is collinearly aligned with the first receptacle 128 and the second receptacle 144 to retain the blood glucose monitor unit in the first position. Additionally, in some embodiments, the top member 114 and base member 112 fully contain the carrier base 102, retaining member 104, and blood glucose monitor unit (e.g., sensor device 106) therein.

All prior patents and publications referenced herein are incorporated by reference in their entireties.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "between" does not necessarily require being disposed directly next to other elements. Generally, this term means a configuration where something is sandwiched by two or more other things. At the same time, the term "between" can describe something that is directly next to two opposing things. Accordingly, in any one or more of the embodiments disclosed herein, a particular structural component being disposed between two other structural elements can be:

disposed directly between both of the two other structural elements such that the particular structural component is in direct contact with both of the two other structural elements;

disposed directly next to only one of the two other structural elements such that the particular structural component is in direct contact with only one of the two other structural elements;

disposed indirectly next to only one of the two other structural elements such that the particular structural component is not in direct contact with only one of the two other structural elements, and there is another element which juxtaposes the particular structural component and the one of the two other structural elements;

disposed indirectly between both of the two other structural elements such that the particular structural component is not in direct contact with both of the two other structural elements, and other features can be disposed therebetween; or any combination(s) thereof.

As used herein "embedded" means that a first material is distributed throughout a second material.

What is claimed is:

1. A packaging system for retaining an annular shaped unit in a vertically aligned position relative to a base plane, the packaging system comprising:
    a carrier base comprising:
        a first receptacle;
    a retaining member comprising:
        a second receptacle, and
        a wedge, wherein the wedge is configured to retain the annular shaped unit in the second receptacle in the vertically aligned position relative to the base plane;

wherein the retaining member is arranged in the first receptacle; and a container comprising:

a base member comprising:

a bottom surface, and at least one first sidewall extending from the bottom surface and defining a first opening therein, wherein the base member is configured to receive the carrier base therein; and a top member comprising:

a top surface, and at least one second sidewall extending from the top surface and defining a second opening therein, wherein the top member is configured to receive the base member therein such that the at least one second sidewall extends around the at least one first sidewall when the top member is positioned onto the base member;

wherein the container is configured to fully contain the carrier base, the retaining member, and the annular shaped unit therein.

2. The packaging system according to claim 1, wherein the second receptacle comprises:

a first bottom surface comprising a concave shape corresponding to the annular shaped unit and configured to enable the annular shaped unit to fully seat into the second receptacle.

3. The packaging system according to claim 1, wherein the retaining member is formed of a material comprising rubber or silicon.

4. The packaging system according to claim 1, wherein the retaining member is formed of a material consisting of rubber or silicon.

5. The packaging system according to claim 1, wherein the wedge is configured to engage an inner surface of the annular shaped unit to retain the annular shaped unit in the vertically aligned position.

6. The packaging system according to claim 1, wherein the packaging system is configured to receive any of a plurality of annular shaped units having different arc lengths and different heights.

7. The packaging system according to claim 1, wherein the top member further comprises:

a third receptacle, wherein the third receptacle is configured to be colinearly aligned with the first receptacle and the second receptacle when the carrier base is arranged into the base member and the top member is positioned onto the base member.

8. The packaging system according to claim 7, wherein the third receptacle comprises:

a second bottom surface comprising a concave shape corresponding to a shape of the annular shaped unit and configured to enable the annular shaped unit to fully seat into the third receptacle.

9. A packaging system for a blood glucose monitor unit comprising a ring shaped body comprising any of a plurality of different arcs and different heights, the packaging system comprising:

a container;

a carrier base comprising:

a first receptacle; and a retaining member comprising:

a second receptacle, wherein the second receptacle comprises a first bottom surface having a concave shape corresponding to a shape of the ring shaped body and configured to enable the blood glucose monitor unit fully seat into the second receptacle, and a wedge, wherein the container is configured to fully contain the carrier base, the retaining member, and the blood glucose monitor unit therein.

10. The packaging system according to claim 9, wherein the wedge is configured to act on an inner surface of the ring shaped body to retain the blood glucose monitor unit in a vertically aligned position relative to a base plane.

11. The packaging system according to claim 9, wherein the retaining member is formed of a material comprising rubber or silicon.

12. The packaging system according to claim 9, wherein the retaining member is formed of a material consisting of rubber or silicon.

13. The packaging system according to claim 9, wherein the first receptacle is configured to receive the retaining member therein.

14. The packaging system according to claim 9, wherein the container comprises:

a base member comprising:

a bottom surface, and at least one first sidewall extending from the bottom surface, and a top member comprising:

a top surface, and at least one second sidewall extending from the top surface, wherein the top member is configured to receive the base member therein such that the at least one second sidewall extends around the at least one first sidewall when the top member is positioned onto the base member.

15. The packaging system according to claim 14, wherein the top member further comprises:

a third receptacle, wherein the third receptacle is configured to be colinearly aligned with the first receptacle and the second receptacle when the carrier base is arranged into the base member and the top member is positioned onto the base member.

16. The packaging system according to claim 15, wherein the third receptacle comprises:

a second bottom surface comprising the concave shape corresponding to the shape of the ring shaped body and configured to enable the blood glucose monitor unit to fully seat into the third receptacle.

17. A method of packaging a blood glucose monitor unit comprising an annular shaped body having an inner circumference, the method comprising:

inserting a retaining member into a first receptacle of a carrier base, the first receptacle configured to hold the retaining member in a first position; and inserting the blood glucose monitor unit into a second receptacle of the retaining member until a wedge extending from a sidewall of the second receptacle is positioned within an aperture of the annular shaped body of the blood glucose monitor unit to hold the blood glucose monitor unit in the first position.

18. The method according to claim 17, further comprising:

inserting the carrier base into a base member, and

US 12,661,202 B2

13 positioning a top member onto the base member so that
the top member extends around a circumference of the
base member and a third receptacle arranged on an
inner surface of the top member is colinearly aligned
with the first receptacle and the second receptacle to 5
retain the blood glucose monitor unit in the first posi-
tion.

19. The method according to claim 18, wherein the top
member and the base member fully contain the carrier base,
the retaining member, and the blood glucose monitor unit 10
therein.

* * * * *

14